United States Patent [19]
Noda et al.

[11] Patent Number: 5,962,649
[45] Date of Patent: Oct. 5, 1999

[54] PROCESS FOR PURIFYING RECOMBINANT HUMAN SERUM ALBUMIN

[75] Inventors: Munehiro Noda; Akinori Sumi; Takao Ohmura; Kazumasa Yokoyama, all of Osaka, Japan

[73] Assignee: Yoshitomo Pharmaceutical Industries, Ltd., Osaka, Japan

[21] Appl. No.: 08/522,089

[22] Filed: Aug. 31, 1995

[30] Foreign Application Priority Data

Aug. 31, 1994 [JP] Japan .................................. 6-207704

[51] Int. Cl.⁶ ...................................................... C07K 1/16
[52] U.S. Cl. .......................... 530/364; 530/412; 530/413; 530/414; 530/415; 530/416; 530/362; 530/363; 435/69.1; 435/69.6
[58] Field of Search .................. 435/69.1, 69.6; 530/362, 363, 364, 412, 413, 415, 414, 416

[56] References Cited

U.S. PATENT DOCUMENTS 5,369,020 11/1994 Sumi et al. ............................ 435/69.6
5,440,018 8/1995 Ohmura et al. ......................... 530/363

FOREIGN PATENT DOCUMENTS

0570916 A2 11/1993 European Pat. Off. .
05709163 5/1993 France .

OTHER PUBLICATIONS

McCreath et al. (1992) J. Chromatog. 597, pp. 189–196.
Burns et al. (1987) Annals of the New York Acad. Sci, vol. 501, pp. 103–107.
Gordon et al. (1990) Biotech. Adv. vol. 8, pp. 741–762.

Biotechnology and Bioengineering, vol. 48, pp. 461–475, 1995, Evans et al., "Countercurrent Gradient Chromatography: A Continuous Focusing Technique."

Annals of the New York Academy of Sciences, 1987, Burns et al., "The Magnetically Stabilized Fluidized Bed as a Biochemical Processing Tool."

Biotechnology Advances, vol. 8, No. 4, pp. 746–762, 1990, Gordon et al., "An Overview Of Continuous Protein Purification Processes."

Journal of Chromatography, 597 (1992), pp. 189–196, McCreath et al., "Novel Affinity Separations Based on Perfluorocarbon Emulsions Use of a Perfluorocarbon Affinity Emulsion for the Purification of Human Serum Albumin From Blood Plasma in a Fluidised Bed."

*Primary Examiner*—Robert A. Wax
*Assistant Examiner*—Enrique D. Longton
*Attorney, Agent, or Firm*—Sughrue, Mion, Zinn, Macpeak & Seas, PLLC

[57] ABSTRACT

The invention provides a process for purifying recombinant human serum albumin (rHSA) by heating a culture medium containing rHSA and the rHSA-producing host cello, feeding said heated solution upwardly into a fluidized bed in which adsorbent particles are suspended to effect contacting with the adsorbent particles and then recovering the adsorbed fraction containing the rHSA, and a composition comprising rHSA which shows a A35D/A280 ratio of below 0.015, when formulated into a 25% solution of said albumin.

8 Claims, 7 Drawing Sheets

FIG. 3 rHSA CULTURE MEDIUM (< pH 6)

- HEATING (68° C, 30 MIN., CONTAINING 10 mM Na CAPRYLATE
- DILUTION (DISTILLED WATER) ELECTRIC CONDUCTIVITY: ABOUT 10 mS
- REGULATED TO pH 4.5

STREAMLINE SP

- WASHING (50 mM Na ACETATE + 50 mM NaCl, pH 4.5)
- ELUTION (100 mM Na PHOSPHATE + 300 mM NaCl, pH 9)

rHSA ELUATE

| INVENTION PROCESS | ABSORBANCE (A350/A280) | ABSORBANCE (A350/A280) | CONVENTIONAL PROCESS |
|---|---|---|---|
| ↓ CULTURE MEDIUM | 0.0475 | 0.0475 | ↓ CULTURE MEDIUM |
|  |  | 0.0639 | ↓ PRESSING |
|  |  | 0.0601 | ↓ ULTRAFILTRATION MEMBRANE TREATMENT 1 |
| ↓ HEATING (68° C, 30 MIN.) | 0.0291 | 0.0353 | ↓ CYSTEINE HT (60° C, 1 HR.) |
| ↓ STREAMLINE SP | 0.0311 | 0.0332 | ↓ ULTRAFILTRATION MEMBRANE TREATMENT 2 |
| ↓ CYSTEINE HT (60° C, 1 HR.) | 0.0212 | 0.0385 | ↓ CATION EXCHANGER TREATMENT |
| ↓ HYDROPHOBIC CHROMATOGRAPHY | 0.0197 ←→ | 0.0390 | ↓ HYDROPHOBIC CHROMATOGRAPHY |
| ↓ ULTRAFILTRATION MEMBRANE TREATMENT | 0.0205 ←→ | 0.0317 | ↓ ULTRAFILTRATION MEMBRANE TREATMENT |
| ↓ DEAE CHROMATOGRAPHY | 0.0128 ←→ | 0.0178 | ↓ DEAE CHROMATOGRAPHY |
| ↓ ULTRAFILTRATION MEMBRANE TREATMENT | 0.0140 ←→ | 0.0204 | ↓ ULTRAFILTRATION MEMBRANE TREATMENT |

FIG. 6

PROCESS FOR PURIFYING RECOMBINANT HUMAN SERUM ALBUMIN

FIELD OF THE INVENTION

This invention relates to a process for easily purifying human serum albumin obtained in high yields by gene manipulation. The present invention also relates to a composition comprising recombinant human serum albumin which shows an extremely low degree of coloring, which is a serious problem characteristic to recombinant human serum albumin.

BACKGROUND OF THE INVENTION

Human serum albumin (hereinafter referred to simply as HSA) is the most abundant protein contained in plasma. It contributes to the maintenance of osmotic pressure in blood and binds to nutrients and metabolites to thereby transport these substances. HSA having these functions has been employed as a drug for treating hypoalbuminemia caused by an albumin loss or reduction in albumin synthesis, and in hemorrhagic shock.

HSA has been produced mainly from a fraction of collected blood. However, the process for producing HSA from blood has such problems as sporadic supply of blood, economical disadvantage, and contamination with undesirable substances such as hepatitis virus. Thus there has been an urgent requirement to develop a material usable as a substitute for naturally occurring USA.

Under these circumstances, techniques for the mass production and purification of HSA by means of gene manipulation (as a substitute for the HSA originating in blood) have been developed as recombinant DNA technology has progressed To purify the HSA obtained by gene manipulation (hereinafter referred to as recombinant HSA and abbreviated as rHSA), it is not appropriate to apply the conventional processes for purifying HSA originating in plasma as such. This is because the impurities to be eliminated from rHSA completely differ from those contained in the HSA originating in plasma. Namely, rHSA is contaminated with, for example, coloring matters characteristic to recombinant HSA, proteins originating in the host cells, polysaccharides, etc. In particular, it is necessary to sufficiently eliminate components originating in the host cells, since they are foreign matters for living organisms including human being and thus can cause a problem of antigenicity.

Accordingly, there have been carried out various studies in order to isolate and purify to a sufficient degree rHSA produced via culture from components originating in the host cells and culture components. One of the conventional processes is exemplified by the process which comprises subjecting a yeast culture medium containing rHSA to pressing—ultrafiltration membrane treatment—heating—ultrafiltration membrane treatment and then treating by procedures such as chromatography using a cation exchanger and an anion exchanger, and hydrophobic chromatography [JP-A-5-317079 (the term "JP-A" as used herein means an "unexamined Japanese patent application") corresponding to EP-A-570916, *Biotechnology of Blood Proteins*, 1993, 227, 293–298]. Further, the process comprising the above-described procedure followed by the chelate resin treatment or the boric acid/borate treatment has been reported (EP-A-570916, JP-A-6-245789 corresponding to EP-A-612761).

In the above-mentioned conventional process, it is essentially required to effect the purification consisting of the above-mentioned several steps to thereby eliminate antigens originating in the host cells and achieve a high degree of purification. On the other hand, this process has such disadvantages as a decrease in the yield of rHSA and a prolonged treating period due to large number of steps. Although attempts have been made to elevate the yield of each step so as to improve the yield of rHSA, it seems that no further improvement in yield can be made and thus the yield of rHSA has already reached the upper limit. Moreover, the conventional process described above suffers from another problem that the pressing is effected in an open system and thus there is a risk of contamination. Namely, hygienic management, which is essentially required in the production of rHSA as a medicine, is highly difficult therein. In addition, the degree of coloring of rHSA can be reduced only to a A350/A280 ratio of about 0.015 (in the case of a solution containing 250 mg/ml of rHSA) at the lowest (JP-A-7-170993 and JP-A-7-170994 corresponding to EP-A-658569). on the other hand, there has been developed a process for recovering a target protein directly from a crudo culture medium without affecting any pre-treatment such as elimination of cells or concentration of the medium, after the completion of the cultivation (e.g., the streamline method with the use of expanded bed adsorption technique developed by Pharmacia, International Publication In Japan No. 6-500050 corresponding to EP-A-538467).

No case has been reported so far on the application of the above-mentioned expanded bed adsorption technique to the purification of rHSA, in particular, the recovery and purification of rHSA from a yeast culture medium. Thus, it remains unknown whether or not such a method is actually useful in the rationalization of the purification of rHSA and the improvement in the yield of the same. However, it is expected that the application of this method or one similar thereto to the purification of rHSA would contribute to the simplification of the conventional purification treatment consisting of several steps.

However, there arises a problem that, under the acidic conditions employed for the adsorption by a streamline column (adsorbent: Streamline SP) for use in the above-mentioned method, rHSA contained in the culture medium is rapidly degraded by proteases contained in the culture medium and thus the yield of rHSA is seriously lowered. It is, therefore, difficult to apply the above-mentioned expanded bed adsorption technique as such to the purification of rHSA.

Thus, there has boon an urgent requirement to develop a process by which rHSA can be highly purified in a stable state at a high yield without spoiling the merits of the expanded bed adsorption technique (i.e., the simplification and rationalization of the purification process, etc.).

SUMMARY OF THE INVENTION

An object of the present invention is to provide a simple process for purifying recombinant HSA to a high purity level and to an excellent quality level within a short period of time. Another object of the present invention is to provide rHSA from which coloring matters characteristic to gene manipulation originating in the host, medium, etc. have been sufficiently eliminated; and a composition comprising the resulting rHSA.

To solve the above-mentioned problems, the present inventors have conducted extensive studies. As a result, they have found that proteases can be easily and effectively inactivated by directly heating a culture medium of an HSA production system in which host cells remain. Based on this finding, they have further found out that when this heated solution is contacted directly with adsorbent particles suspended in a fluidized bed without removing the cells therefrom, rHSA can be easily purified at a high yield. They have furthermore found out that the combination of the above-mentioned heating treatment with the adsorbent particle treatment makes it possible to reduce the number of steps of the conventional process for purifying rHSA from five (i.e., pressing—ultrafiltration membrane treatment—heating—ultrafiltration membrane treatment—cation exchanger treatment) to two (heating—adsorbent particle treatment), thus significantly shortening the purification period while elevating yield.

Moreover, the present inventors have found that their process makes it possible to obtain rHSA, which is substantially free from any impurities originating in the host cells and thus exhibits a substantially lowered degree of coloring compared with the one obtained by the conventional process.

Accordingly, the present invention relates to a process for purifying rHSA which comprises heating a culture medium containing rHSA and the rHSA-producing host, contacting the heated solution with adsorbent particles suspended in a fluidized bed and recovering the adsorbed fraction. More particularly, it relates to a process for purifying rHSA which comprises heating a culture medium containing rHSA and an rHSA-producing host, feeding the heated solution upward into a fluidized bed in which adsorbent particles are suspended to effect contacting the heated solution with the adsorbent particles, then reversing the flow direction and feeding downward a buffer to elute and recover the rHSA adsorbed by the adsorbent particles.

The present invention further relates to a purification process wherein a culture medium of an rHSA-producing host is heated to a temperature of from 50 to 100° C. for from 1 minute to 10 hours, a process for purifying rHSA wherein a heated solution is contacted with adsorbent particles at a pH value of from about 3 to 5 in an atmosphere of an electric conductivity of from 0.1 to 50 mS, and a process for purifying rHSA wherein adsorbent particles are those having a strong cation exchange group.

The present invention further relates to a process for purifying rHSA wherein an adsorbed fraction containing rHSA, which has been recovered from the fluidized bed by the above-mentioned purification process, is subjected to at least one purification treatment selected from a group consisting of hydrophobic chromatography, anion exchanger treatment, chelate resin treatment, boric acid/borate treatment and ultrafiltration membrane treatment, preferably after heating in the presence of a reducing agent.

The present invention furthermore relates to a composition comprising recombinant human serum albumin which shows a A350/A280 ratio of below 0.015, when formulated into a 25% solution of the albumin (i.e., rHSA concentration: 250 mg/ml).

BRIEF DESCRIPTION OF THE DRAWINGS

FIG. 7(a–d) are chromatograms showing the results of GPC-HPLC analysis of rHSA obtained by the process of the present invention (absorbance: measured at 280 nm).

In these figures, each symbol has the following meaning.

A: control.
B: 68° C., 30 minutes, pH 6.0 .
C: 68° C., 30 minutes, pH 6.8.
D: 68° C., 30 minutes, pH 7.5.
E: 68° C., 30 minutes, pH 8.2.
F: 60° C., 2 hours, pH 6.0.
G: 60° C., 2 hours, pH 6.8.
H: 60° C., 2 hours, pH 7.5.
I: 60° C., 2 hours, pH 8.2.
J: 60° C., 2 hours, pH 6.8, 10 mM cysteine.
K: 60° C., 2 hours, pH 7.5, 10 mM cysteine.
L: room temperature (25° C.), 2 hours, pH 6.0.
M: room temperature (25° C.), 2 hours, pH 8.2.
1: rHSA purified by the conventional process (pressing—membrane—heating—membrane—cation exchanger—hydrophobic chromatography—anion exchanger treatment) followed by the chelate resin treatment.
2; rHSA resulting after the anion exchanger (DEAE) treatment in accordance with the process of Example 1.
3: rHSA resulting after the chelate resin treatment in accordance with the process of Example 1.

DETAILED DESCRIPTION OF THE INVENTION (1) HSA obtained by gene manipulation

In the present invention, the HSA-producing host obtained by gene manipulation is not particularly restricted, so long as it has been prepared by gene manipulation. Namely, either those which have been reported in publicly known literatures or those which will be developed in future my be appropriately selected therefor. More particularly, such a list is exemplified by HSA-producing microorganisms obtained by gene manipulation (*Escherichia coli*, yeasts, *Bacillus subtilis*, etc.) and animal cells. It is particularly preferable to use yeasts, in particular, those belonging to the genus Saccharomyces (for example, *S. cerevisiae*) or Pichia (for example, *P. pastoris*) as the host. Also, auxotrophic strains and antibiotic-sensitive strains are usable therefor. It is still preferable to use *Saccharomyces cerevisiae* AH22 strain (a, his 4, leu 2, can 1) or *Pichia pastoris* GTS115 strain (his 4).

Preparation of HSA-producing host, production of rHSA by its culturing and isolation and recovery of rHSA from the cultured broth are all carried out in accordance with known methods which may be modified slightly. For example, preparation of an HSA-producing host may be effected using a process in which a natural HSA gene is used (JP-A-58-

56684 corresponding to EP-A-73646, JP-A-58-90515 corresponding to EP-A-79739 and JP-A-58-150517 corresponding to EP-A-91527), a process in which a modified human serum albumin gene is used (JP-A-62-29985 and JP-A-1-98486 corresponding to EP-A-206733), a process in which a synthetic signal sequence is used (JP-A-1-240191 corresponding to EP-A-329127), a process in which a serum albumin signal sequence is used (JP-A-2-167095 corresponding to EP-A-319641), a process in which a recombinant plasmid is introduced into a chromosome (JP-A-3-72889 corresponding to EP-A-399455), a process in which hosts are fused (JP-A-3-53877 corresponding to EP-A-409156), a process in which a mutation is generated in a methanol containing medium, a process in which a mutant $AOX_2$ promoter is used (EP-A-506040), a process in which HSA is expressed in *B. subtilis* (JP-A-62-215393 corresponding to EP-A-229712), a process in which HSA is expressed in yeast (JP-A-60-41487 corresponding to EP-A-123544, JP-A-63-39576 corresponding to EP-A-248657 and JP-A-63-74493 corresponding to EP-A-251744) and a process in which HSA is expressed in Pichia (JP-A-2-104290 corresponding to EP-A-344459).

Of these methods, the method in which mutation is induced in a methanol-containing medium is carried out in the following manner. A transformant of an appropriate host, preferably a Pichia yeast, illustratively a strain GT5115 (NRRL deposition No. Y-15851), is obtained in the usual manner by introducing a plasmid, containing a transcription unit by which HSA is expressed under the control of the $AOX_1$ promoter, into the $AOX_1$ gene region of the host (cf. JP-A2-104290). This transformant hardly grows in a medium containing methanol. In consequence, this transformant is cultured in a methanol-containing medium to generate mutation, and a strain capable of growing in the medium is isolated Methanol concentration in the medium may range, for example, from 0.0001 to 5%. The medium may be either synthetic or natural. The culturing may be carried out, for example, at a temperature of from 15 to 40° C. for approximately from 1 to 1,000 hours.

Culturing of the HSA-producing host may be effected by each of the methods disclosed in the above patents, by a method in which producer cells and the product are obtained in high concentrations by a fed-batch culture (a semi-batch culture) which method is carried out by gradually supplying a high concentration solution of glucose, methanol or the like in appropriate small amounts to avoid high concentration substrate inhibition against the producer cells (JP-A-3-83595) or by a method in which the HSA productivity is improved by the addition of fatty acids to the culture medium (JP-A-4-293495 corresponding to EP-A-504823 and U.S. Patent 5,334,512).

A medium usually employed in the art supplemented with a fatty acid having from 10 to 26 carbon atoms or a-salt thereof can be used as a medium for culturing a transformed host, and culturing of the transformant can be carried out under known conditions. The medium may be either synthetic or natural, but preferably is a liquid medium. For example, a suitable synthetic medium may be composed of: carbon sources, such as various saccharides; nitrogen sources, such as urea, ammonium salts, nitrates; trace nutrients, such as various vitamins, nucleotides; and inorganic salts, such as of Mg, Ca, Fe, Na, K, Mn, Co and Cu. An illustrative example of such a medium is YNB liquid medium, which consists of 0.7% Yeast Nitrogen Baso (Difco) and 2% glucose. An illustrative example of a useful natural medium is YPD liquid medium, which consists of 1% Yeast Extract (Difco), 2% Bacto Peptone (Difco) and 2% glucose. The medium pH may be neutral, weakly basic or weakly acidic. In the case of a methylotrophic host, the medium may be further supplemented with methanol in an amount of approximately from 0.01 to 5%.

The culturing temperature preferably ranges from 15 to 43° C. (20 to 30° C. for yeast, 20 to 37° C. for bacterium). The culturing period ranges from 1 to 1,000 hours, preferably 20 to 360 hours, by means of static or shake culturing or batch, semi-batch or continuous culturing under agitation and aeration. It is desirable to prepare a seed culture prior to the batch culturing by means of static or shake culturing or batch, semi-batch or continuous culturing under agitation and aeration. The seed culturing may be carried out using the aforementioned YNB liquid medium or YPD liquid medium, preferably at 30° C. (for yeast) or 37° C. (for bacterium) and for 10 to 100 hours.

(2) Purification of rHSA
(i) Heating treatment

In the process for purifying rHSA according to the present invention, the culture medium of the HSA-producing host obtained in the above-mentioned cultivation step can be directly heat-treated while containing the host cells and without effecting any separation procedure such as centrifugation or ultrafiltration membrane treatment. That is to say, the heating treatment is carried out at a first step in the purification process of the present invention.

Heating is performed usually at 50 to 100° C. for 1 minute to 10 hours, preferably at 60 to 80° C. for 20 minutes to 3 hours and still preferably at 68° C. for 30 minutes. It is preferable to perform this treatment in the presence of a stabilizer. Examples of the stabilizer include acetyltryptophan, organic carboxylic acids having 6 to 18 carbon atoms and salts thereof. These stabilizers may be used together. Acetyltryptophan is added in such an amount as to give a final concentration of, for example, about 1 to 100 mM. Examples of the organic carboxylic acids having 6 to 18 carbon atoms include caproic acid, caprylic acid, capric acid, lauric acid, palmitic acid and oleic acid. It is preferable to use 10 mM of caprylic acid. Examples of the salts thereof include alkali metal salts (sodium salt, potassium salt, etc.) and alkaline earth metal salts (calcium salt, etc.). These organic carboxylic acids having 6 to 18 carbon atoms or salts thereof may be added in an amount of, for example, about 1 to 100 mM.

To suppress the coloration caused by heating, it is effective to add about 1 to 100 nm, preferably 5 to 30 mM, of a thiol compound (e.g., mercaptoethanol, cysteine, reduced glutathione, etc.) and, preferably to further add 10 to 1,000 mM of aminoguanidine in tho heating step (JP-A-3-103188).

In the conventional process, either a supernatant (filtrate) or cells obtained by centrifuging or filtering a host culture medium are heated. This is because it is feared that when a culture medium containing cells is directly heated, the leakage of impurities, lipids, nucleic acids, proteases, etc. would exert undesirable effects on the purification of the target substance. Thus, it has been unknown whether direct heating of a culture medium containing cells is effective for purification of the target substance or not.

According to the present invention, however, it has been revealed that when the culture medium containing the rHSA and the host cells is directly heated, neither the structural function of rHSA nor the yield thereof is deteriorated but the powerful proteases contained in the culture medium can be effectively inactivated Thus the process for the inactivation of the proteases can be simplified. Moreover, HSA obtained by gene manipulation can be effectively purified by the process as will be described hereinafter.

(ii) Dilution of heated solution and adjustment of its properties

The heated solution obtained in the above (i) is then treated with adsorbent particles suspended in a fluidized bed. Prior to this treatment, it is preferable to dilute the heated solution so as to contact this heated solution with the adsorbent particles in an atmosphere of an electric conductivity of from 0.1 to 50 mS, preferably from 0.5 to 35 mS and still preferably from 5 to 15 mS. As will be described in Test Example 3 hereinafter, the amount of rHSA binding to the adsorbent particles increases as the dilution of the heated solution is elevated and the electric conductivity of the atmosphere, at which the heated solution is contacted with the adsorbent particles, is lowered, and attains the maximum level at an electric conductivity of around 8 to 12 mS. The solvent to be used as the diluent is not particularly restricted, so long as the structural function of rHSA in the heated solution is not thereby deteriorated. It may be appropriately selected while taking the adsorption conditions into consideration. The diluent is exemplified by an acetate buffer of a concentration of 50 mM or below and by distilled water. From the viewpoint of convenience, it is preferable to use distilled water.

Next, the pH value of the solution is regulated to an acidic level, which is suitable for the adsorption by the adsorbent particles. It is adjusted to usually from pH 3 to 5, preferably from pH 4 to 4.8 and more preferably about pH 4.5. Although any acidic solution may be used for the regulation of pH without restriction, it is preferable to use acetic acid.

(iii) Adsorbent particle treatment

Following the dilution and adjustment of the pH value, the resulting heated solution is contacted with the adsorbent particles Examples of the adsorbent particles include a carrier having a cation exchange group (i.e., a cationic adsorbent), such as adsorbent particles of the sulfo group type or carboxyl group type. Adsorbent particles of the sulfo group type are exemplified by sulfo-agarose (Streamline SP, S-Sepharose, both manufactured by Pharmacia), sulfo-cellulose (S-Cellulofine, manufactured by Chisso Corporation), sulfopropyl-agarose (SP-Sepharose, manufactured by Pharmacia), SP-Cellthru-Big Beads (manufactured by Sterogene), sulfopropyl-dextran (SP-Sephadex, manufactured by Pharmacia) and sulfopropyl-polyvinyl (SP-Toyopearl, manufactured by Tosoh Corporation). Adsorbent particles of the carboxyl group type are exemplified by carboxymethyl-agarose (CM-Cellthru-Big Beads, manufactured by Sterogene), carboxymethyl-dextran (CM-Sephadex, manufactured by Pharmacia) and carboxymethyl-cellulose (CM-Cellulofine, manufactured by Chisso Corporation). It is preferable to use strongly cationic adsorbent particles of the sulfo group type, with Streamline SP (manufactured by Pharmacia) particularly preferred.

The particle size of the adsorbent particles usually ranges from, for example, 30 to 1,100 μm, preferably from 100 to 300 μm.

The contact can be effected at a pH value of from about 3 to 5, preferably from about 4 to 4.8 and more preferably about 4.5, and at a salt concentration of from about 0.01 to 0.2M, preferably from about 0.05 to 0.1M.

It is preferable to preliminarily equilibrate the adsorbent particles under such contact conditions as described above. More particularly, it is preferable to equilibrate the adsorbent particles with a 50 mM acetate buffer (pH 4.5) containing 50 mM of sodium chloride.

The adsorbent particles are usually equilibrated and the sample is injected into the fluidized bed containing the adsorbent particles, contacted with the adsorbent particles and then eluted from the fluidized bed in accordance with the following procedure.

Namely, the above-mentioned adsorbent particles are first packed into an appropriate column and allowed to sink. Then an equilibration buffer is fed upward from the bottom port of the column to thereby suspend the adsorbent particles. In this step, the flow rate of the buffer flowing upward in the column serves as the counterbalance to the adsorbent particles sedimenting due to gravity and thus the adsorbent particles are uniformly suspended in an equilibrated state (i.e., a so-called fluidized bed). Into the column, in which the above-mentioned fluidized bed has been formed, the crude culture medium containing the cells, which has been treated according to the above (i) heating and (ii) dilution steps, is supplied upwardly from the bottom port of the column. Then the target rHSA binds to the adsorbent particles, while fine particles and impurities originating in the host cells or the culture medium pass as such among the adsorbent particles in the fluidized bed and are thus discarded from the top port of the column. Also, impurities loosely binding to the adsorbent particles are washed away with the washing buffer which is successively and upwardly supplied. It is preferable that these procedures are performed in accordance with the expanded bed adsorption technique [*Journal of Chromatography*, 597 (1992), 129–145].

As the washing buffer, an equilibration buffer is employed.

The target protein, i.e., rHSA is recovered by reversing the flow direction and feeding downwardly an elution buffer from the top port of the column. Elution of rHSA can be carried out at the pH value ranging from about 8 to 10, preferably from about 8.5 to 9.5 and more preferably about 9, and at the salt concentration ranging from about 0.2 to 0.5%, preferably from about 0.3 to 0.4M. A particular example of the elution buffer 16 a 0.1M phosphate buffer (pH 9) containing 0.3M of sodium chloride.

The above-mentioned operations including equilibration of the adsorbent particles, injection of the sample into the fluidized bed containing the adsorbent particles, contact with the adsorbent particles, elution from the fluidized bed, etc. can be easily and efficiently carried out at a high reproducibility by using a Streamline System (manufactured by Pharmacia) provided with a Streamline column (adsorbent: Streamline SP, manufactured by Pharmacia).

Thus rHSA having a high purity can be obtained. The purity of the rHSA obtained by the above-mentioned treatment with the adsorbent particles is almost comparable to that of the rHSA obtained by the conventional process consisting of several steps including pressing—ultrafiltration membrane treatment—heating—ultrafiltration membrane treatment—cation exchanger treatment. Moreover, rHSA can be obtained in a stable form (i.e., without being degraded) at a high yield owing to the heating of the culture medium prior to the treatment with the adsorbent particles. Accordingly, the present invention makes it possible to reduce the number of steps of the above-mentioned conventional process for purifying rHSA from five to two and thus largely shorten the purification period. The present invention further makes it possible to elevate the yield of rHSA from the culture medium, compared with the conventional process.

The rHSA obtained by these treatments can be further purified by a conventional purification process. Examples of the purification process to be used herein include those commonly employed in the art such as hydrophobic chromatography, ultrafiltration membrane treatment, anion exchanger treatment, chelate resin treatment and boric acid/borate treatment. Either one of these treatments or a combination thereof may be used. In order to obtain a purified rHSA product of improved qualities, it is preferable to perform the hydrophobic chromatography, ultrafiltration membrane treatment, anion exchanger treatment, ultrafiltration membrane treatment, chelate resin treatment, boric acid/borate treatment and ultrafiltration membrane treatment in this order.

Prior to the above-mentioned purification, it is preferable to heat again the adsorbed fraction eluted after contacting the solution with the adsorbent particles in the presence of a reducing agent. As will be shown in Test Example 6 hereinafter, this heating treatment is highly effective in lowering the degree of coloring characteristic of rHSA, though the yield of rHSA is not affected thereby as compared with the case that this heat treatment is omitted. Namely, this heating treatment makes it possible to significantly eliminate the coloring matters by the subsequent purification procedure.

The heating temperature is usually from 50 to 100° C., preferably from about 60 to 80° C. and more preferably 60° C. The heating period is usually from 10 minutes to 10 hours, preferably from about 30 minutes to 5 hours and more preferably 1 hour.

The reducing agent to be used herein is not particularly restricted, so long as it has a reducing effect. Examples thereof include low molecular weight compounds having an SH group (e.g., cysteine, cyateamine, cystamine, methionine, glutathione, etc.), sulfites, pyrosulfites, phosphorous pyrosulfites and ascorbic acid. Cysteine is preferably used. Regarding the addition level, for example, cysteine may be added in such an amount as to give a final concentration of about 1 to 100 mM, while a sulfite may be added in such an amount as to give a final concentration of about 0.001 to 10%.

It is preferable to perform this treatment in the presence of a stabilizer. Examples of the stabilizer include acetyltryptophan and organic carboxylic acid having 6 to 18 carbon atoms or salts thereof. These stabilizers may be used together. Acetyltryptophan may be added, for example, in such an amount as to give a final concentration in the solution of about 1 to 100 mM. Examples of the organic carboxylic acids having 6 to 18 carbon atoms include caproic acid, caprylic acid, capric acid, lauric acid, palmitic acid and oleic acid. It is preferable to use 10 mM of caprylic acid. Examples of the salts thereof include alkali metal salts (e.g., sodium salt, potassium salt, etc.) and alkaline earth metal salts (e.g., calcium salt, etc.). These organic carboxylic acids having 6 to 18 carbon atoms or salts thereof may be added in an amount of, for example, about 1 to 100 mM. By further adding 10 to 1,000 mM of aminoguanidine, the coloration due to heating can be suppressed .(JP-A-3-103188).

(a) Hydrophobic chromatography

The hydrophobic chromatography can ba performed in a conventional manner. Examples of the carrier for hydrophobic chromatography include insoluble carriers having an alkyl group carrying 4 to 18 carbon atoms (butyl group, octyl group, octyldecyl group, etc.) or a phenyl group. It is preferable to use one having a phenyl group such as phenyl-cellulose (Phenyl-Cellulofine, manufactured by Chisso Corporation). In this step, rHSA can be recovered into the unadsorbed fraction. The contact may be performed, for example, at about pH 6 to 8, preferably at about pH 6.5 to 7, and at a salt concentration of about 0.01 to 0.5M, preferably about 0.05 to 0.2M.

(b) Anion exchanger treatment

The anion exchanger treatment may also be performed in a conventional manner. Any anion exchanger may be used, so long as it is an insoluble carrier having an anion exchange group. Examples of the anion exchange group include a diethylaminoethyl (DEAE) group and a quaternary aminoethyl (QAE) group. It is preferable to use one having a DEAE group such as DEAE-agarose (DEAE-Sepharose, manufactured by Pharmacia), DEAE-dextran (DEAE-Sephadex, manufactured by Pharmacia) and DEAE-polyvinyl (DEAE-Toyopearl, manufactured by Tosoh Corporation). In this step, rHSA can be recovered into the unadsorbed fraction. The contact may be performed, for example, at about pH 6 to 8, preferably at about pH 6.5 to 7, and at a salt concentration of about 0.01 to 0.1M.

By this anion exchanger treatment, coloring matters and trace impurities can be eliminated.

(c) Ultrafiltration membrane treatment

After the completion of the hydrophobic chromatography and/or the anion exchanger treatment, the rHSA-containing fraction thus recovered is preferably subjected to the ultrafiltration membrane treatment. By this ultrafiltration membrane treatment, pyrogens can be eliminated. In the ultrafiltration membrane treatment, it is preferable to use an ultrafiltration membrane having a molecular weight cutoff of from 100 to 300K. As a particular example thereof, a Pellicon cassete membrane 100K (manufactured by Millipore) may be cited.

(d) Chelate resin treatment

The chelate resin treatment is effective particularly in eliminating coloring matters which are characteristic to HSA obtained by gene manipulation. In the above-mentioned purification process, this treatment is preferably carried out following the hydrophobic chromatography—ultrafiltration membrane treatment—anion exchanger treatment—ultrafiltration membrane treatment. It is performed by contacting a chelate resin having a specific ligand with rHSA and the rHSA is obtained in the passed fraction. It is preferable that the carrier part of the chelate resin is one having hydrophobic properties. Examples thereof include a styrene/divinylbenzene copolymer and an acrylic acid/methacrylic acid copolymer. On the other hand, examples of the ligand part of the chelate resin include polyol groups such as N-methylglucamine, polyamine groups (including polyalxylene polyamines such as polyethylene polyamine) having plural imino groups, amino groups, ethyleneimino groups, etc. in the molecule and thiourea groups. It is convenient to use commercially available those having a styrene/divinylbenzene copolymer carrier, such as DIAION CRB02 (ligand: N-methylglucamine group, manufactured by Mitsubishi Kasei Corporation), LEWATIT TP214 (ligand:—$NHCSNH_2$, manufactured by Bayer) and Amberlite CG4000.

Appropriate conditions for this chelate resin treatment are as follows.

pH: acidic or neutral or basic (pH 3,to 9, preferably pH 4 to 7).

Period: 1 hour or longer, preferably 6 hours or longer.

Ionic strength: 50 mmho or below, preferably from 1 to 10 mmho.

Mixing ratio: 0.1 to 100 g, preferably 1 to 10 g (wet basis) of resin per 250 mg of HSA.

(e) Boric acid/borate treatment

By further treating the rHSA-containing solution, which has been obtained by the above-mentioned treatment, with boric acid or a borate (referred to as boric acid/borate heroin), impurities having an antigenicity originating in the host and nonantigenic free impurities detectable by the phenol-sulfuric acid method can be eliminated.

Examples of the boric acid usable herein include orthoboric acid, metaboric acid and tetraboric acid. Examples of the borate include alkali metal salts (e.g., sodium salt, potassium salt, etc.) and alkaline earth metal salts (e.g., calcium salt, etc.). It is preferable to use calcium tetraborate. The boric acid or borate may be added in such an amount as to give a final concentration of from about 0.01 to 1M, preferably from about 0.05 to 0.2M. This treatment is performed, for example, at about pH 8 to 11, preferably about pH 9 to 10, for about 1 to 100 hours, preferably about 5 to 50 hours. In this step, the rHSA-containing solution having a low electric conductivity is more desirable. For example, the electric conductivity of the rHSA-containing solution is 1 mS or below. Also, the rHSA-containing solution having a high rHSA concentration is more desirable. For example, the rHSA concentration is 5% or more, preferably from about 15 to 25%.

After the completion of the above-mentioned boric acid/borate treatment, rHSA is recovered from the supernatant by a conventional method such as centrifugation or ultrafiltration.

(3) Properties of highly purified HSA originating in gene manipulation

The highly purified rHSA thus obtained is a homogeneous substance having a molecular weight of about 67,000 and an isoelectric point of 4.9. It consists of monomers alone, being substantially free from dimers, polymers or decomposition products (molecular weight: about 43,000). Also it is substantially free from any antigenic impurities or polysaccharides originating in the producer host. When formulated into an rHSA solution of 250 mg/ml (a 25% solution), it has a A350/A280 ratio of below 0.015, preferably 0.013 or below and more preferably from about 0.01 to 0.015. rHSA having such reduced degree of coloring (i.e., a low A350/A280 value) can be obtained by using an appropriate combination of the known purification techniques [the above-mentioned techniques (a) to (e), etc.].

The present invention makes it possible for the first time to provide recombinant HSA (or a composition containing the same) showing a A350/A280 ratio of below 0.015, when formulated into a 25% solution of rHSA.

(4) Formulation

The rHSA obtained by the process of the present invention can be formulated into preparations by known methods (ultrafiltration membrane treatment, addition of stabilizer, antiseptic filtration, pipetting, freeze-drying, etc.). The rHSA preparations thus obtained may be applied to clinical purposes as serum albumin preparations in the same dose and in the same manner as those employed in the case of the conventional HSA originating in plasma. They are also usable as stabilizers, fillers or carriers for drugs.

The term an "rHSA-containing composition" as used herein means a material which contains the high purity rHSA of the present invention at a high concentration but lower than 100% together with other component(s) in a trace amount.

To further illustrate the present invention in greater detail, and not by way of limitation, the following Examples will be given.

EXAMPLE 1

(1) Heating treatment of culture medium

An HSA-producing yeast Pichia pastoris was acquired and incubated in accordance with the method described in EP-A-655503.

About 2.8 liter of the culture medium including cells thus obtained was heated to 68° C. for 30 minutes as such. The heating treatment was performed in the presence of 10 mM of sodium caprylate. This culture medium had a pH value of 6. Next, the heated solution was quickly cooled to about 15° C. and diluted about 2-fold with distilled water (total volume: 5.5 liter). Then the pH value thereof was regulated to 4.5 with an acetic acid solution.

(2) Adsorbent particle treatment (Streamline SP treatment)

To a Streamline SP column (C50, 5×100 cm, gel volume; 300 ml, manufactured by Pharmacia), which had been equilibrated with a 50 mM acetate buffer (pH 4.5) containing 50 mM of sodium chloride, was fed upwardly 5.5 liter of the culture medium (electric conductivity: <10 mS) containing the yeast cells which had been obtained by the above-mentioned heating treatment (1). The feeding was made at a flow rate of 100 cm/h under stirring. Next, the same buffer (2.5 times by volume as much as the column capacity) as the one employed for the equilibration of the column was fed upwardly into the column to thereby wash the column at a flow rate of 100 cm/h for 1 hour and then at 300 cm/h for 30 minutes. Subsequently, the flow direction was reversed and an eluent [a 100 mM phosphate buffer (pH 9) containing 300 mm of sodium chloride, flow rate: 50 cm/h] was fed into the column. Thus a fraction containing rHSA was obtained.

The rHSA-containing fraction thus eluted was detected by measuring the absorbance at 280 nm.

(3) Heating treatment

The rHSA-containing fraction thus obtained was heated at 60° C. for 1 hour in the presence of 10 mM of cysteine, 5 mM of sodium caprylate and 100 mM of aminoguanidine hydrochloride at pH 7.5.

(4) Hydrophobic chromatography

The rHSA solution heated in the above (3) was poured into a column packed with Phenyl-Cellulofine (5×25 cm, gel volume: 500 ml, manufactured by Chisso Corporation) which had been equilibrated with a 50 mM phosphate buffer (pH 6.8) containing 0.15M of sodium chloride. Under these conditions, the rHSA was not adsorbed by the Phenyl-Cellulofine column but passed therethrough. The rHSA-containing solution passing through the column was concentrated to a volume of about 0.2 liter using an ultrafiltration membrane having a molecular weight cutoff of 30,000 (manufactured by Millipore) and the rHSA-containing solution was replaced by a 50 mM phosphate buffer (pH 6.8).

(5) Anion exchanger treatment

After the completion of the hydrophobic chromatography, the rHSA-containing solution, which had been concentrated and buffer-replaced, was poured into a column packed with DEAE-Sepharose FF (5×25 cm, gel volume: 500 ml, manufactured by Pharmacia) which had been equilibrated with a 50 mM phosphate buffer (pH 6.8). Under these conditions, the rHSA was not adsorbed by the DEAE-Sepharose column but passed therethrough. The rHSA passing through the column was concentrated to a volume of about 0.2 liter using an ultrafiltration membrane having a molecular weight cut-off of 30,000 (manufactured by Millipore) and the rHSA-containing solution was replaced by distilled water.

(6) Chelate resin treatment

To 0.2 liter of the purified rHSA having a concentration of about 7% was added acetic acid to thereby regulate the pH value to 4.5. Then it was poured into a column packed with DIAION CRB02 (5×2.5 cm, gel volumes 500 ml, manufactured by Mitsubishi Kasei Corporation), which had been equilibrated with a 50 mM sodium acetate buffer (pH 4.5), and circulated overnight. Under these conditions, the rHSA was not adsorbed by the gel but passed through the column.

(7) Boric acid/borate treatment

The rHSA concentration was adjusted to 2.5%, while the electric conductivity of the solution was regulated to 1 mS or below. Sodium tetraborate was added thereto to give a final concentration of 100 mM. Next, calcium chloride was added thereto to give a final concentration of 100 mM, while maintaining the pH value at 9.5. After allowing to stand for about 10 hours, the precipitate thus formed was removed and the supernatant was recovered, concentrated and desalted. Then it was concentrated by using an ultrafiltration membrane having a molecular weight cutoff of 30,000 (manufactured by Millipore) and subjected to buffer replacement. If necessary, stabilizers (sodium caprylate and acetyltryptophan) were added followed by filter sterilization using a 0.22 μm filter (manufactured by Millipore). The resulting rHSA solution can be used for injection.

TEST EXAMPLE 1

Stabilizing effect of heating treatment on rHSA culture medium

It is known that potent proteases contained in an rHSA culture medium degrade rHSA. As Table 1 shows, the degradation of rHSA proceeds extremely quickly under acidic conditions of pH 4.

TABLE 1 pH stability of rHSA culture medium

Figure 1:
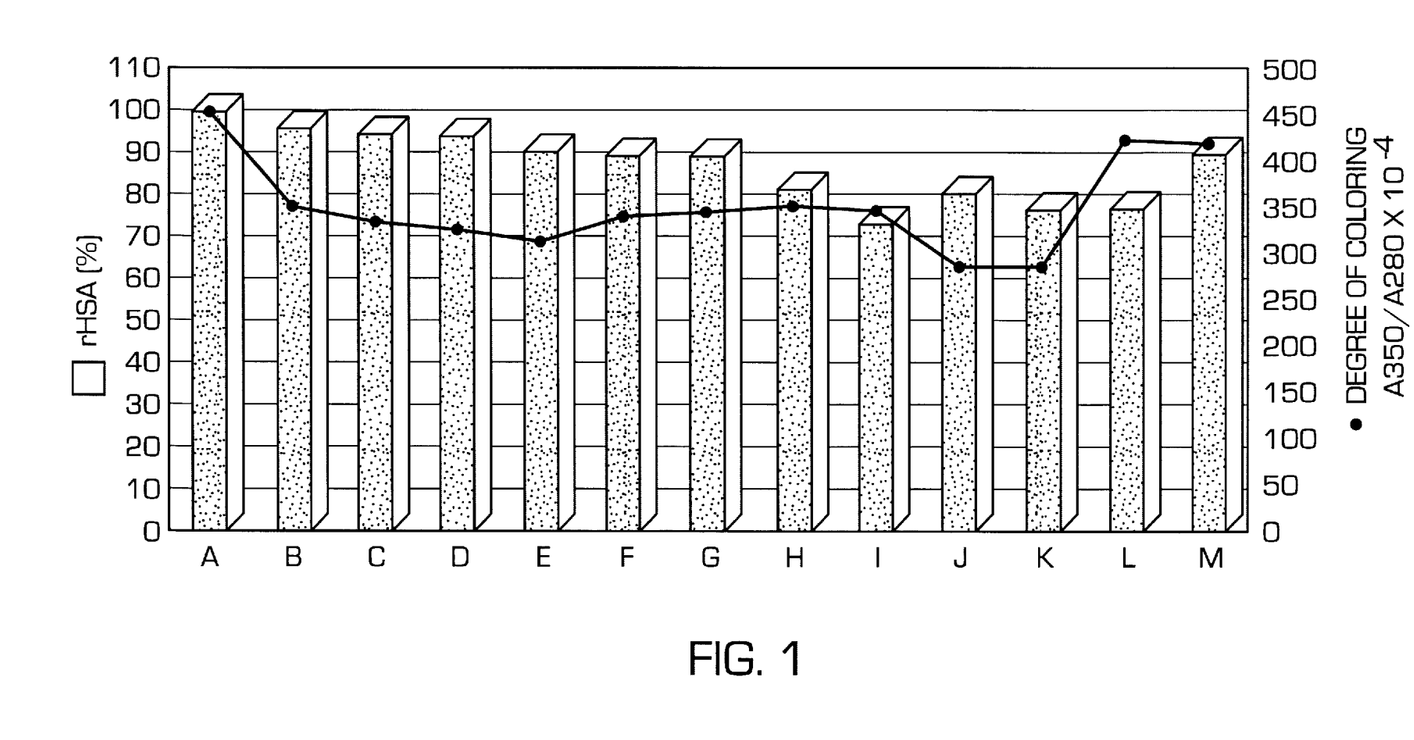
FIG. 1 is a graph which shows the stabilization effect of the heating treatment on an rHSA culture medium.

| Sample | Storage Condition | Storage pH value | HSA conc. (mg/ml) | Yield (%) |
|---|---|---|---|---|
| culture medium (containing yeast cells) | 15° C., 15 hr (stationary) | control | 7.6 | 100.0 |
| | | 6.0 | 7.7 | 100.9 |
| | | 4.5 | 7.2 | 94.0 |
| | | 4.0 | 3.0 | 39.9 | rHSA was adsorbed by Streamline SP at about pH 4.5. Thus the stability of rHSA at about pH 4.5 was examined and heating conditions effective for inactivation of proteases as a pre-treatment for maintaining rHSA in a stable state were examined by determining the stability of rHSA after adjusting the pH value of the heated solution to 4.5 and allowing it to stand at room temperature overnight. FIG. 1 shows the results. In the heating stop, sodium caprylate was added to each sample to give a final concentration of 10 mM. The heating conditions employed are as follows.

A: control.
B: 68° C., 30 minutes, pH 6.0.
C: 68° C., 30 minutes, pH 6.8.
D: 68° C., 30 minutes, pH 7.5.
E: 68° C., 30 minutes,, pH 8.2.
F: 60° C., 2 hours, pH 6.0.
G: 60° C., 2 hours, pH 6.8.
H: 60° C., 2 hours, pH 7.5.
I: 60° C., 2 hours, pH 8.2.
J: 60° C., 2 hours, pH 6.8, 10 mM of cysteine.
K: 60° C., 2 hours, pH 7.5, 10 mM of cysteine.
L: room temperature (25° C.), 2 hours, pH 6.0.
M: room temperature (25° C.), 2 hours, pH 8.2.

As a result, it was more effective to heat to 68° C. for 30 minutes than to heat to 60° C. for 2 hours. Regarding the pH value, the most desirable results were obtained at around pH 6, which was the initial pH value of the culture medium to be heated.

TEST EXAMPLE 2

Relationship between pH value of rHSA culture medium and binding ability to adsorbent The pH value of the culture medium (rHSA: 55.6 mg) was adjusted to various levels (pH 4.5 to 4.9) with acetic acid followed by the addition of 1 ml of a Streamline SP gel equilibrated with a 50 mM acetate buffer. After mixing and stirring at room temperature for 1 hour and washing with each equilibration buffer, the amount (%) of the rHSA remaining in the unadsorbed fraction was determined. As a result, it was found out that the amount of the rHSA binding to the adsorbent increased with a decrease in the pH value and attained tho maximum at around pH 4.5 (Table 2).

TABLE 2 pH value of rHSA culture medium and binding ability to gel

| Sample (adsorption condition) | rHSA in unadsorbed fraction (mg) | rHSA in unadsorbed fraction (%) |
|---|---|---|
| starting material | 55.6 | 100.0 |
| no gel added: pH 4.5 | 51.0 | 91.7 |
| 1 ml of gel added: | | |
| pH 4.5 | 5.1 | 9.2 |
| pH 4.6 | 7.6 | 13.7 |
| pH 4.7 | 14.9 | 26.8 |
| pH 4.8 | 33.1 | 59.5 |
| pH 4.9 | 49.4 | 88.8 |

TEST EXAMPLE 3

Figure 2:
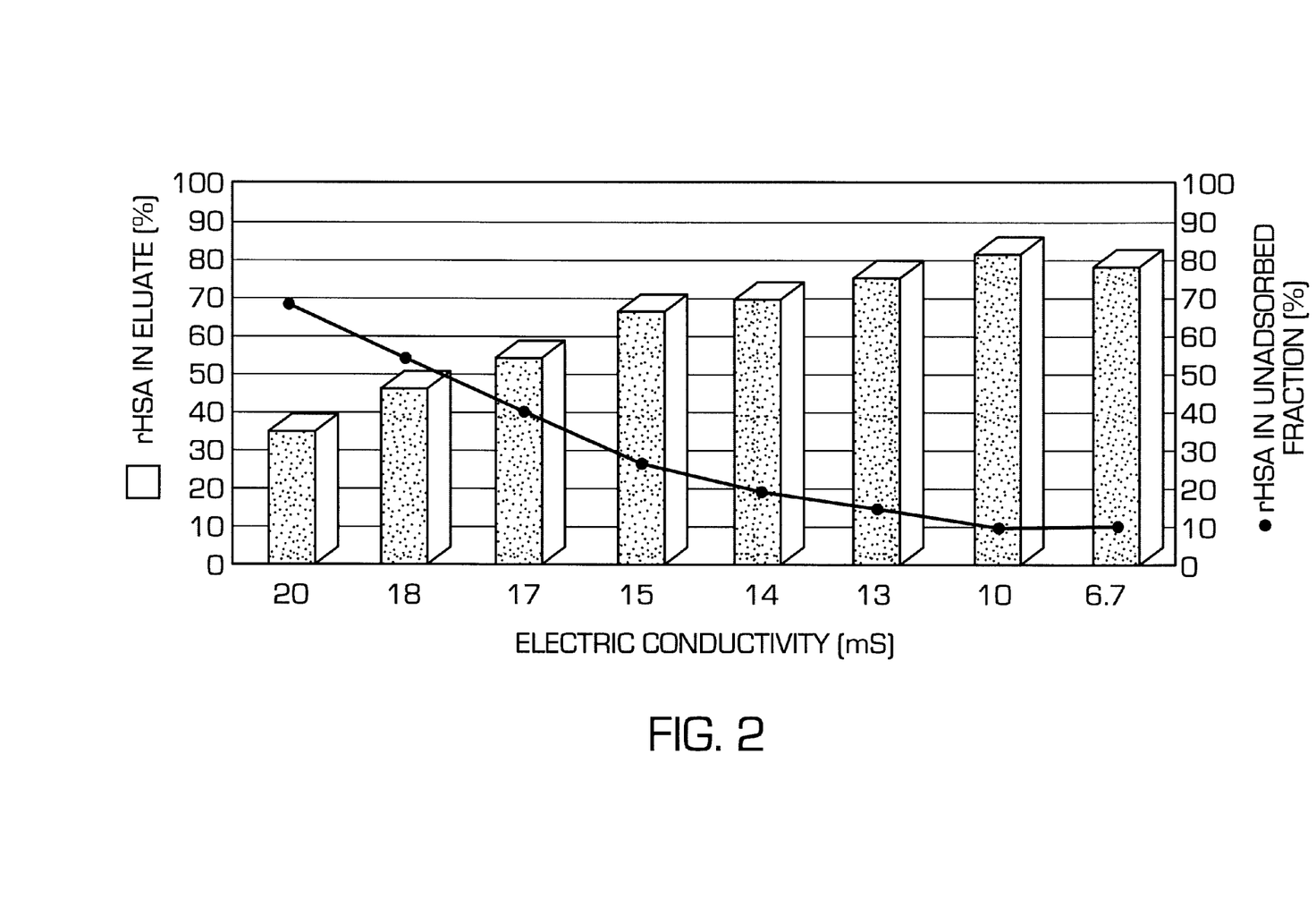
FIG. 2 is a graph which shows a relationship between the electric conductivity under the atmosphere where the heated solution is contacted with the adsorbent particles, and the ability of rHSA to bind to the adsorbent particles.

Relationship between electric conductivity of atmosphere for the contact of heated solution with adsorbent particles and binding ability of rHSA to adsorbent particles After heating, the culture medium [electric conductivity: about 20 mS (at 25° C.), rHSA: 47.1 mg] was diluted with distilled water to give various dilutions and the pH value of each dilution was regulated to 4.5 with acetic acid followed by the addition of 1 ml of a Streamline SP gel which had been equilibrated with a 50 mM acetate buffer (pH 4.5) containing 50 mM of sodium chloride. After mixing at room temperature for 1 hour and washing with the equilibration buffer, rHSA was eluted with a 0.1M phosphate buffer (pH 9) containing 0.3M of sodium chloride. As a result, it was found out that the amount of rHSA binding to the adsorbent particles increased with an increase in the dilution and a decrease in the electric conductivity of the solution and attained the maximum level at the electric conductivity of the atmosphere (in the gel mixture), in which the heated solution was contacted with the adsorbent particles, of about 8 to 12 mS (FIG. 2).

TEST EXAMPLE 4

Stability of Streamline SP eluate

The culture medium was diluted 2-fold with distilled water and the pH value was adjusted to 4.5 with acetic acid. Then a definite amount of a Streamline SP gel, which had been equilibrated with a 50 mM acetate buffer (pH 4.5) containing 50 mM of sodium chloride, was added thereto and the mixture was stirred at room temperature for 1 hour. Next, the gel was washed with the equilibration buffer and rHSA was eluted by using a 0.1M phosphate buffer (pH 9) containing 0.3M of sodium chloride. Then the stability of the rHSA in the fraction (pH 8) was examined. As a result, the rHSA in the culture medium which had been preliminarily heated (68° C., 30 minutes) showed no change after 3 days, while the rHSA originating in the untreated culture medium was reduced to about 50 % due to degradation (Table 3).

TABLE 3

Stability of Streamline SP eluate
(room temperature, 3 days, pH 8)

| Sample | rHSA before storage (mg/ml) | rHSA after storage (mg/ml) | Residual rate (%) |
|---|---|---|---|
| eluate from unheated rHSA culture | 4.39 | 2.44 | 55.7 |
| eluate from heated rHSA culture (60° C., 2 hr) | 4.55 | 4.45 | 97.6 |
| eluate from heated rHSA culture (68° C., 30 min) | 4.52 | 4.67 | 103.4 |

TEST EXAMPLE 5

Figure 3:
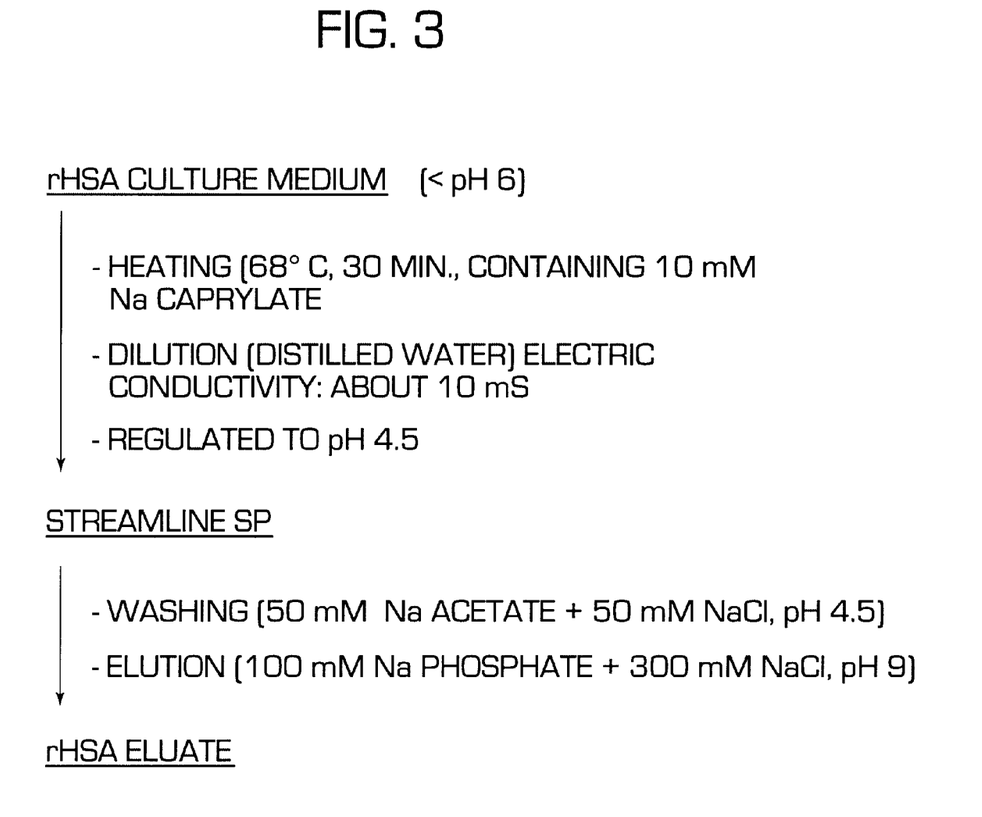
FIG. 3 is a flow chart which shows the optimum flow of the purification of rHSA front a culture medium (containing yeast cells) with the use of Streamline SP.

Comparison of rHSA yield and degree of coloring between (heating—adsorbent particle) treatment and (no heating—adsorbent particle) treatment Based on the results of Test Examples 1 to 4, an optimum flow of the heating—adsorbent particle treatment process was established (FIG. 3).

In accordance with the flow of FIG. 3, an attempt was made to purify rHSA from a culture medium (2.8 liter) containing yeast cells using a Streamline SP column (5×100 cm, gel volume: 300 ml). On the other hand, a culture medium (2.7 liter) containing yeast cells was subjected to the treatment with the adsorbent particles without initially heating to thereby purify rHSA.

Figure 4A:
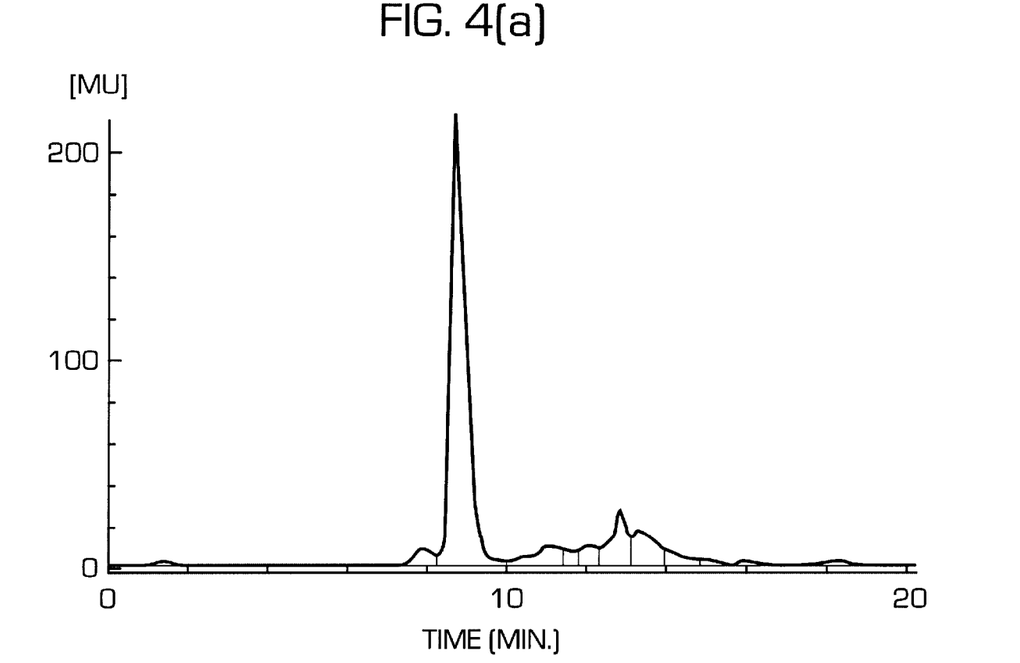
FIG. 4 shows a gel filtration HPLC profile of a Streamline SP eluate including the heating step (heating—adsorbent particle) treatment [(a)] and that of a Streamline SP eluate without the heating step (no heating—adsorbent particle) treatment [(b)] (absorbance: measured at 280 nm).
Figure 4B:
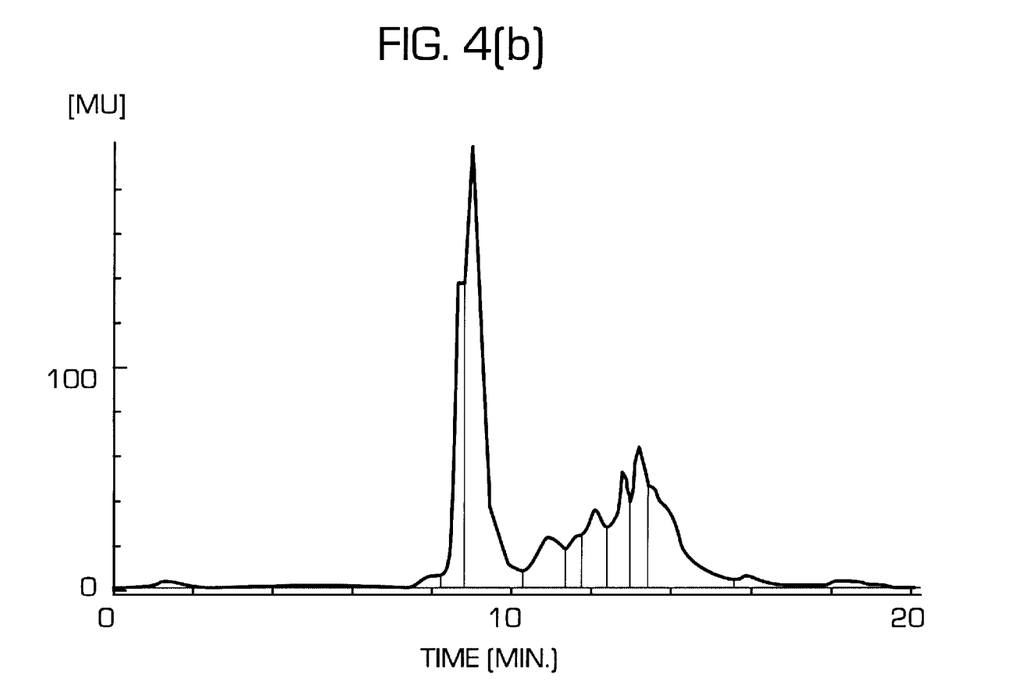

As a result, the total yield achieved by the (no heating—adsorbent particle) treatment was 50%, while a higher total yield (about 85%) was achieved by the (heating—adsorbent particle) treatment of the present invention. Also, the rHSA obtained by the (no heating—adsorbent particle) treatment showed a degree of coloring of 0.048 in terms of A350/A280, while the rHSA obtained by the (heating—adsorbent particle) treatment of the present invention showed a lower degree of coloring (0.0345) (Table 4). FIG. 4 shows a comparison between a gel filtration HPLC profile of an Streamline eluate in the (heating—adsorbent particle) treatment and that of an Streamline SP eluate in the (no heating—adsorbent particle) treatment. The latter shows serious decomposition and degradation of rHSA.

TABLE 4

Purification of rHSA by Streamline SP column

| Sample | Volume (liter) | rHSA (g) | Yield (%) | Degree of coloring (A350/A280) |
|---|---|---|---|---|
| heated sample: | | | | |
| culture medium | 2.8 | 19.3 | 100 | 0.0475 |
| heated (68° C., 30 min) | 5.5 | 17.5 | 90.5 | 0.0291 |
| column pass | 10.5 | 1.3 | 6.6 | — |
| column eluate | 1.2 | 16.5 | 85.4 | 0.0345 |
| unheated sample: | | | | |
| culture medium | 2.7 | 11.9 | 100 | 0.0482 |
| solution added to column (diluted, pH-adjusted) | 5.3 | 10.0 | 84.2 | 0.0366 |
| column pass | 10.5 | 1.0 | 8.8 | — |
| column eluate | 1.2 | 5.9 | 50.0 | 0.0480 |

TEST EXAMPLE 6

Effect of heating with cysteine on degree of coloring of rHSA The rHSA eluate from the Streamline SP column in the (heating—adsorbent particle) treatment of the above Table 4, which was used as a starting material, was subjected to the hydrophobic chromatography and anion exchanger treatment described in Example 1 (4) and (5) and thus the degree of coloring (A350/A280) was evaluated. In this evaluation, two samples of the Streamline SP eluates, i.e., one resulted from heating in the presence of cysteine (final concentration: 10 mM) and the other resulted from non-heating in the presence of cysteine were employed. As a result, the rHSA yields of these two samples were almost the same regardless of the presence of cysteine. Regarding the degree of coloring, however, the sample which had been heated in the presence of cysteine showed 0.0128, which was significantly lower compared with 0.0184 of the unheated sample, after the anion exchanger treatment (Table 5).

TABLE 5

Purification of rHSA after the Streamline step

| Sample | Degree of coloring (A350/A280) |
|---|---|
| Streamline eluate | 0.0311 |
| heated with cysteine | 0.0212 |
| phenyl-treated | 0.0197 |
| ultrafiltered (UF30K-R) | 0.0205 |
| DEAE-treated | 0.0128 |
| Streamline eluate | 0.0311 |
| phenyl-treated | 0.0270 |
| ultrafiltered (UF30K-R) | 0.0275 |
| DEAE-treated | 0.0184 |

TEST EXAMPLE 7

Figure 5:
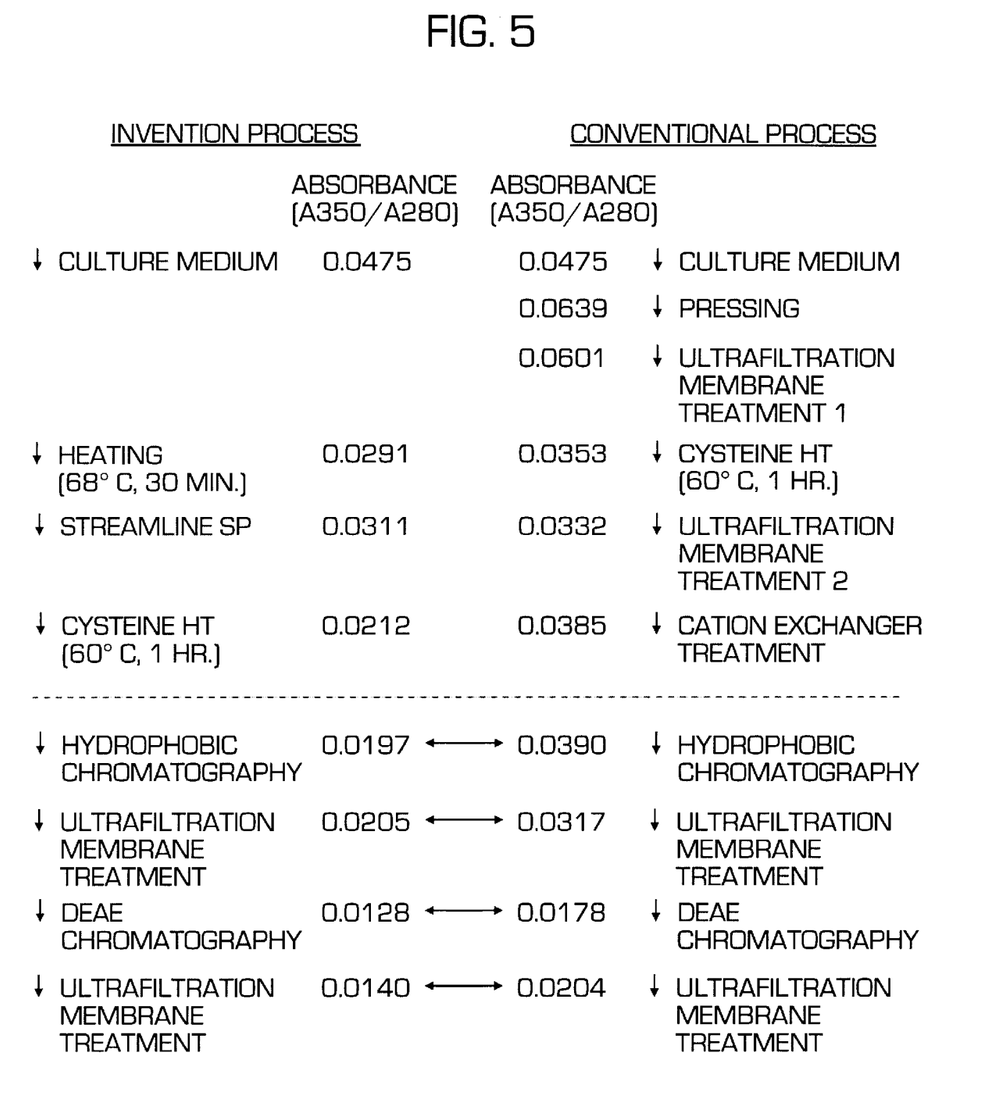
FIG. 5 shows a comparison between the conventional process and the process of the present invention by monitoring changes in the degree of coloring (A350/A280) of rHSA at each step.
Figure 6:
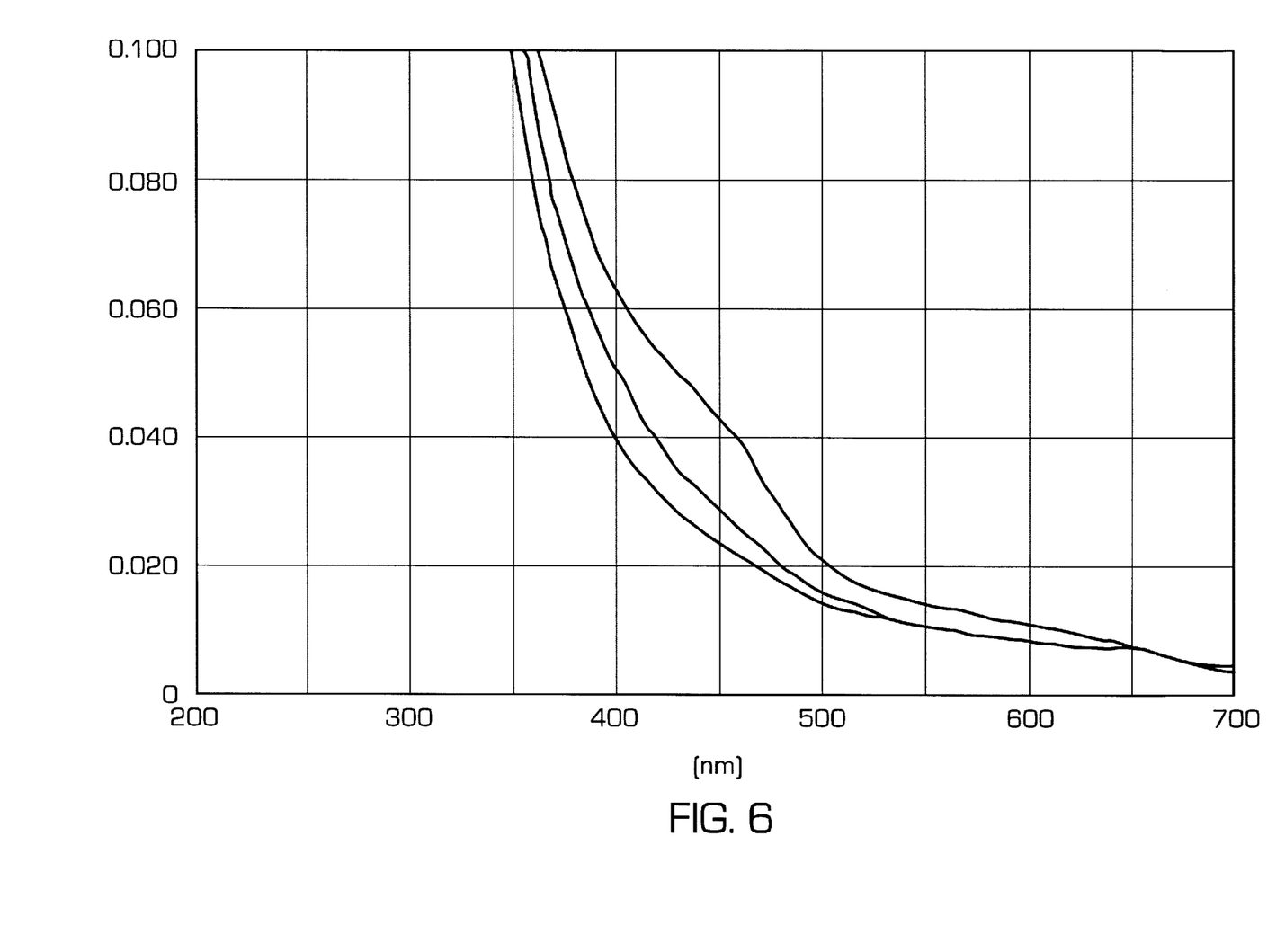
FIG. 6 is absorption spectra of rHSA obtained by the process of the present invention as compared with rHSA obtained by the conventional process.

Reduction in degree of coloring (A350/A280) of rHSA by introducing Streamline SP treatment FIG. 5 shows a comparison of changes in the degree of coloring (A350/A280) between rHSA at each step in the conventional process and rHSA in a process of the present invention, which included the Streamline SP step, until the step of the anion exchanger treatment. In the process of the present invention wherein the Streamline SP treatment was employed and heating was effected immediately thereafter in the presence of cysteine, a large difference from the conventional process was observed at the step of hydrophobic chromatography. After the completion of the anion exchanger treatment, an extremely low degree of coloring (0.0128) was observed. FIG. 6 shows a comparison of the absorption spectrum between a sample resulting after the chelate resin treatment following the conventional process as shown in FIG. 5 (curve 1) and samples resulting after the anion exchanger treatment and the chelate resin treatment of the purification process of the present invention as described in Example 1 (curve 2 and 3). As a result, the absorption spectrum of the rHSA purified by the process of the present invention already showed a ramarkably low pattern over the visible region (350–700 nm) after the anion exchanger treatment, compared with the sample resulting after the chelate resin treatment following the conventional process as shown in FIG. 5. After treating with the chelate resin in the inventive process, this difference became more obvious.

TEST EXAMPLE 8

Figure 7:
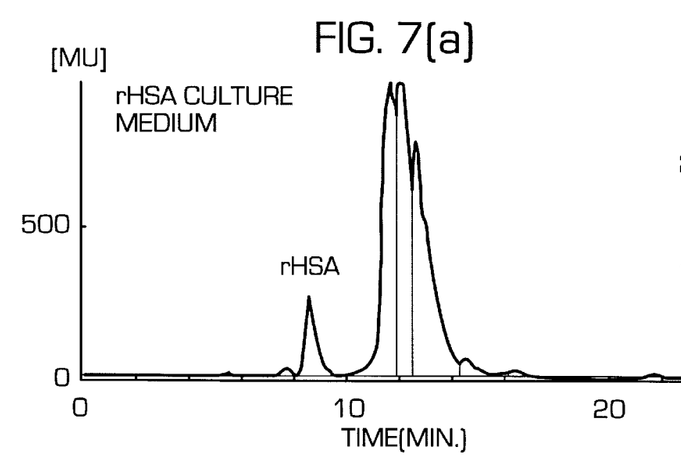

Analysis of rHSA resulting from the process of the present invention by gel filtration HPLC FIG. 7 shows the results of gel filtration high performance liquid chromatography (GPC-HPLC) analysis of the rHSA samples which resulted after stated steps of the process of the present invention as described in Example 1 (rHSA culture medium, Streamline SP eluate, Streamline SP unadsorbed fraction, DEAE-post-treated fraction). As a result, it was clarified that high molecular weight substances other than rHSA and low molecular weight substances contained in the culture medium had been mostly washed away together with the yeast cells into the Streamline SP unadsorbed fraction at a high efficiency and albumin was specifically recovered into the eluate. The HPLC pattern of the sample prepared by using this fraction as a starting material and further purifying by the anion exchanger (DEAE) treatment showed a sharp peak of albumin (HSA monomer) alone. Thus its purity was comparable or even superior to the sample resulted from the DEAE step of the conventional purification process.

On the basis of these Test Examples, the rHSA yield resulted from the DEAE step of the conventional purification process and that resulted from the DEAE concentration step in the process involving the adsorbent particle (Streamline SP) treatment step were calculated and compared with each other. In the process involving the adsorbent particle (Streamline SP) treatment, the number of the steps was reduced from five of the conventional process (i.e., pressing—membrane—heating—membrane—cation exchanger treatment) to two. Thus the treatment time was largely shortened and the yield was increased by 30%.

TEST EXAMPLE 9

Analysis of impurities originating in host

The culture medium of a yeast which did not produce albumin was purified in the same manner as the process of the present invention as described in Example 1. Then a rabbit was immunized therewith, By using the antiserum thus obtained, testing was carried out for detecting impurities originating in the yeast in the purified albumin solution. Enzyme immunoassay (EIA) was employed therefor. The albumin concentration of the sample was adjusted to 250 mg/ml.

As a result, no antigenic impurity originating in the yeast was detected from the purified albumin resulted after the boric acid/borate treatment at a detection limit of 0.1 ng/ml

TEST EXAMPLE 10

Properties of rHSA of the present invention purified by the process of Example 1
(1) Molecular weight The molecular weight was determined by the abovementioned HPLC gel filtration method. The rHSA purified in accordance with the process of the present invention had a molecular weight of about 67,000, i.e., almost the same as that of the HSA originating in plasma.
(2) Isoelectric point The isoelectric point was determined in accordance with the method of Allen et al. [*J. Chromatog.*, 146, 1 (1978)] with the use of a polyacrylamide gel. The rHSA purified in accordance with the process of the present invention had an isoelectric point of about 4.9, i.e., almost the same as that of the HSA originating in plasma.
(3) Degree of coloring The degree of coloring was determined by using a solution of the purified rHSA (albumin concentration: 250 mg/ml), measuring the absorbance of this solution at 280 and 350 nm and calculating the A350/A280 ratio. The rHSA purified in accordance with the process of the present invention showed an extremely low degree of coloring (A350/A280) of about 0.012.

EXAMPLE 2

(1) Heating treatment of culture medium

About 1,000 liter of the culture medium including cells obtained by the method described in EP-A-655503 in the same manner as in Example 1 was heated to 68° C. for 30 minutes as such. The heating treatment was performed in the presence of 10 mM of sodium caprylate. This culture medium had a pH value of 6. Next, the heated solution was cooled to about 25° C. and diluted about 2-fold with distilled water (total volume: about 2,000 liter). Then the pH value thereof was adjusted to 4.5 with an acetic acid solution (99.7%) in an amount of about 1.1% (v/v) of the volume of the culture medium before dilution.
(2) Adsorbent particle treatment (Streamline SP treatment)

To a Streamline SP column (C1000, 100×110 cm, gel volume: 150 liter, manufactured by Pharmacia), which had been equilibrated with a 50 mM acetate buffer (pH 4.5) containing 50 mM of sodium chloride, was fed upwardly 2,000 liter of the culture medium containing the yeast cells which had been obtained by the above-mentioned heating treatment (1). The feeding was made at a flow rate of 100 to 250 cm/h under stirring so that the cells might not precipitate until the addition of the culture medium to the column was completed. Next, the same buffer (5 times by volume as much as the column capacity) as the one employed for the equilibration of the column was fed upwardly into the column to thereby wash the column at a flow rate of 100 to 500 cm/h. Subsequently, the flow direction was reversed and an eluent [a 100 mM phosphate buffer (pH 9) containing 300 mM of sodium chloride, flow rate: 50 to 100 cm/h] was fed into the column. Thus a fraction containing rHSA was obtained.

The rHSA-containing fraction thus eluted was detected by measuring the absorbance at 280 nm.
(3) Heating treatment The rHSA-containing fraction thus obtained was heated at 60° C. for 1 hour in the presence of 10 mM of cysteine, 10 mM of sodium caprylate, sodium oleate in an amount of 4 moles per mole of rHSA and 100 mM of aminoguanidine hydrochloride at pH 7.5 to reduce the degree of the coloring of rHSA and accelerate the conversion of dimer to monomer.

Table 6 shows the results of four runs using 1 ton of the culture medium respectively. The average yield after the heat treatment of 68° C. for 30 minutes and the heat treatment with cysteine is 98.6% and 88.4%, respectively. The total yield of the four runs shows such a good result as 87.1%, which is in well agreement with the results of Example 1 in which the column of the experimental scale (C50) was used. Thus, it has been confirmed that the process of the present invention is reproducible in a large scale.

TABLE 6

| Run No. | Step | Volume (liter) | rHSA (g) | Yield (%) | Degree of Coloring (A350/A280) |
| --- | --- | --- | --- | --- | --- |
| 1 | culture medium | 922 | 5868 | 100.0 | 0.0596 |
|  | heated (68° C., 30 min) | 1900 | 5399 | 92.0 | 0.0379 |
|  | column pass | 6000 | — | — | — |
|  | column eluate | 200 | — | — | — |
|  | heated with cysteine | 62 | 4840 | 82.5 | 0.0268 |
| 2 | culture medium | 943 | 6246 | 100.0 | 0.0547 |
|  | heated (68° C., 30 min) | 1960 | 6351 | 101.7 | 0.0375 |
|  | column pass | 6400 | — | — | — |
|  | column eluate | 300 | — | — | — |
|  | heated with cysteine | 61 | 5674 | 90.9 | 0.0248 |
| 3 | culture medium | 937 | 6200 | 100.0 | 0.0539 |

TABLE 6-continued

| Run No. | Step | Volume (liter) | rHSA (g) | Yield (%) | Degree of Coloring (A350/A280) |
|---|---|---|---|---|---|
| | heated (68° C., 30 min) | 1877 | 6261 | 101.1 | 0.0307 |
| | column pass | 5777 | 462 | 7.4 | — |
| | column eluate | 200 | — | — | — |
| | heated with cysteine | 111 | 5594 | 90.2 | 0.0227 |
| 4 | culture medium | 916 | 6845 | 100.0 | 0.0520 |
| | heated (68° C., 30 min) | 1885 | 6818 | 99.6 | 0.0556 |
| | column pass | 5885 | — | — | — |
| | column eluate | 300 | — | — | — |
| | heated with cysteine | 111 | 5804 | 84.8 | 0.0235 |

REFERENCE EXAMPLE 1

Determination of rHSA (evaluation of yield)

In the above Test Examples 1 to 8 and 10, the rHSA was quantitatively evaluated (including the yield) by subjecting an rHSA-containing solution to gal filtration HPLC. The detailed elution conditions are as follows.

The solution containing rHSA was poured into a TSK-Gel G3000 SWxL column (0.78×30 cm, manufactured by Tosoh Corporation) which had been equilibrated with a 50 mM sodium phosphate buffer (pH 6.5) containing 0.1% of $NaN_3$ and 0.3% of NaCl. Then rHSA was eluted by using the equilibration buffer as a eluent at a flow rate of 1 ml/min and determined by measuring the absorbance at 280 nm and 350 nm.

The present invention has been completed on the basis of a finding that proteases can be easily and effectively inactivated by directly heating a culture medium containing yeast as such. Thus, the present invention provides a process for easily and effectively purifying rHSA by heating a culture medium in which yeast cells remain and contacting the heated solution directly with adsorbent particles suspended in a fluidized bed. Thus the number of the steps is reduced from five of the conventional process (including pressing—membrane—heating—membrane—cation exchanger treatment) to two stops of heating—adsorbent particle treatment. Thus the treatment period is largely shortened and the yield is elevated. Moreover, the problem of coloration characteristic to recombinant HSA can be solved by the purification process of the present invention whereby coloring matters causing coloration can be efficiently eliminated.

According to the purification process of the present invention, furthermore, the whole process of producing recombinant HSA including the steps of from the cultivation of cells to the purification can be performed on a closed system line, thus bringing about such advantages that the production of HSA can be automated and that hygienic management, which is essentially required in the production of rHSA as a medicine, can be easily effected.

Accordingly, the process of the present invention is highly useful as a process for purifying rHSA which makes it possible not only to shorten the treatment period and to elevate the yield but also to improve the qualities of the product.

In addition, the present invention makes it possible to provide rHSA which does not contain impurities relating to the producer host or the like, and which exhibits sufficiently suppressed coloration for usefulness as a drug.

While the instant invention has been described in detail and with reference to specific embodiments thereof, it will be apparent to one skilled in the art that various changes and modifications can be mace therein without departing from the spirit and scope thereof.

What is claimed is:

1. A process for purifying recombinant human serum albumin which comprises:

heating a culture medium containing said albumin and recombinant human serum albumin-producing host cells to inactivate a protease in said culture medium, contacting said heated culture medium with adsorbent particles suspended in a fluidized bed under conditions for selectively adsorbing said albumin and recovering the adsorbed fraction; and subjecting said recovered adsorbed fraction to at least one treatment selected from the group consisting of heat treatment in the presence of a reducing agent, hydrophobic chromatography, anion exchanger treatment, chelate resin treatment, boric acid/borate treatment and ultrafiltration membrane treatment;

said purified recombinant human serum albumin having an A350/A280 ratio of below 0.015, as measured in a 250 mg/ml solution of said human serum albumin.

2. A process for purifying recombinant human serum albumin as claimed in claim 1, which comprises heating a culture medium containing said albumin and recombinant human serum albumin-producing host cells, feeding said heated solution upward into a fluidized bed in which adsorbent particles are suspended to effect contacting said heated culture medium with the adsorbent particles under conditions for selectively adsorbing said albumin, then reversing the flow direction and feeding downward a buffer to elute and recover the adsorbed fraction.

3. A process for purifying recombinant human serum albumin as claimed in claim 1 or 2, wherein the heating is carried out at from 50 to 100° C. for from 1 minute to 10 hours.

4. A process for purifying recombinant human serum albumin as claimed in claim 3, wherein the heated culture medium is contacted with the adsorbent particles at a pH value of from about 3 to 5.

5. A process for purifying recombinant human serum albumin as claimed in claim 4, wherein said heated culture medium is contacted with said adsorbent particles in an atmosphere of an electric conductivity of from 0.1 to 50 mS.

6. A process for purifying recombinant human serum albumin as claimed in claim 5, wherein said adsorbent particles have a strong cation exchange group.

7. A process for purifying recombinant human serum albumin, wherein an adsorbed fraction containing human serum albumin, which has been recovered by a purification process as claimed in claim 1 or 2, is further subjected to at least one purification treatment selected from a group consisting of hydrophobic chromatography, anion exchanger treatment, chelate resin treatment, boric acid/borate treatment and ultrafiltration membrane treatment.

8. A process for purifying recombinant human serum albumin, wherein an adsorbed fraction containing human serum albumin, which has been recovered by a purification process as claimed in claim 1 or 2, is heated in the presence of a reducing agent to accomplish further decolorizing of said recombinant human serum albumin and then subjected to at least one purification treatment selected from a group consisting of hydrophobic chromatography, anion exchanger treatment, chelate resin treatment, boric acid/borate treatment and ultrafiltration membrane treatment, said process resulting in an A350/A280 ratio of below 0.015, as measured in a 250 m/ml solution of said human serum albumin.

* * * * *